United States Patent [19]

Hoffmann et al.

[11] 4,237,124
[45] Dec. 2, 1980

[54] COMBATING PESTS WITH O-ETHYL-S-N-PROPYL-N-ALKYLAMINO-METHYLIDENE THIOLPHOSPHORIC ACID DIESTER-IMIDES

[75] Inventors: Hellmut Hoffmann, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 54,062

[22] Filed: Jul. 2, 1979

[30] Foreign Application Priority Data

Jul. 20, 1978 [DE] Fed. Rep. of Germany ....... 2831934

[51] Int. Cl.³ .......................... A01N 57/28; C07F 9/24
[52] U.S. Cl. .................................. 424/211; 260/944
[58] Field of Search .......................... 260/944; 424/211

[56] References Cited

U.S. PATENT DOCUMENTS 3,801,679  4/1974  Hoffman et al. .................... 424/211
4,153,604  5/1979  Bader et al. .......................... 260/944
4,176,181  11/1979  Hoffmann et al. ................... 260/944

FOREIGN PATENT DOCUMENTS 2014027  3/1970  Fed. Rep. of Germany .......... 260/959
590612  8/1977  Switzerland ............................ 260/945

*Primary Examiner*—Anton H. Sutto
*Attorney, Agent, or Firm*—Sprung, Felfe, Horn, Lynch & Kramer

[57] ABSTRACT

O-Ethyl-S-n-propyl-N-alkylamino-methylidene thiolphosphoric acid diester-imides of the formula

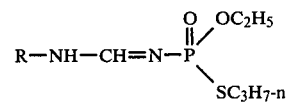

in which R is alkyl, which possess arthropodicidal and nematicidal properties.

8 Claims, No Drawings

COMBATING PESTS WITH O-ETHYL-S-N-PROPYL-N-ALKYLAMINO-METHYLIDENE THIOLPHOSPHORIC ACID DIESTER-IMIDES

The present invention relates to and has for its objects the provision of particular new O-ethyl-S-n-propyl-N-alkylamino-methylidene-thiophosphoric acid diesterimides which possess arthropodicidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known that certain O,S-dialkyl-N-acetyl-thiolphosphoric acid ester-amides, for example O-methyl- and O-ethyl-S-methyl-N-acetyl-thiolphosphoric acid esteramide, have insecticidal and acaricidal properties (see DE-OS (German Published Specification) No. 2,014,027).

It is also known that certain O,S-dialkyl-N-aminomethylidene-thiolphosphoric acid diester-imides, in particular O,S-dimethyl-N-aminomethylidene-thiolphosphoric acid diester-imides, for example O,S-dimethyl-N-(N-pyridin-2-yl-aminomethylidene)-thiolphosphoric acid diester-imide, are insecticidally and acaricidally active (see DE-OS (German Published Specification) No. 2,211,338). However, the action of these compounds is not always satisfactory, especially at low concentrations and when low amounts are used.

The present invention now provides, as new compounds, the O-ethyl-S-n-propyl-N-aminomethylidene-thiolphosphoric acid diester-imides of the general formula $$R-NH-CH=N-P\diagup_{SC_3H_7\text{-}n}^{\diagdown OC_2H_5} \quad (I)$$

in which R represents alkyl.

Preferably, R represents straight-chain or branched alkyl with 1 to 5 (especially with 1 to 3) carbon atoms.

Surprisingly, the O-ethyl-S-n-propyl-N-aminomethylidene-thiolphosphoric acid diester-imides according to the invention exhibit a considerably better action when combating pests, in particular a better insecticidal, acaricidal and nematicidal action, than the known compounds of analogous structure and the same type of action.

The products according to the invention thus represent a valuable enrichment of the art.

The invention also provides a process for the preparation of an O-ethyl-S-n-propyl-N-aminomethylidenethiolphosphoric acid diester-imide of the formula (I), in which an O-ethyl-S-n-propyl-N-alkoxymethylidenethiophosphoric acid diester-imide of the general formula $$R^1-O-CH=N-P\diagup_{SC_3H_7\text{-}n}^{\diagdown OC_2H_5} \quad (II),$$

in which $R^1$ represents $C_1$-$C_4$ alkyl, is reacted with an amine of the general formula $$R-NH_2 \quad (III),$$

in which R has the meaning stated above, if appropriate in the presence of a diluent.

If, for example, O-ethyl-S-n-propyl-N-ethoxymethylidene-thiolphosphoric acid diester-imide and methylamine are used as starting materials, the reaction of these compounds can be outlined by the equation which follows:

$$CH_3NH_2 + C_2H_5-O-CH=N-P\diagup_{SC_3H_7\text{-}n}^{\diagdown OC_2H_5} \xrightarrow{-C_2H_5OH}$$

$$CH_3NH-CH=N-P\diagup_{SC_3H_7\text{-}n}^{\diagdown OC_2H_5}$$

Formula (II) provides a definition of the O-ethyl-S-n-propyl-N-alkoxymethylidene-thiolphosphoric acid diesterimides to be used as starting materials. Preferably, in this formula, $R^1$ represents alkyl with 1 to 3 carbon atoms, especially methyl or ethyl.

Specific examples which may be mentioned are: O-ethyl-S-n-propyl-N-methoxymethylidene- and O-ethyl-S-n-propyl-N-ethoxymethylidene-thiolphosphoric acid diester-imide.

The starting compounds of the formula (II) have not hitherto been described in the literature. They are obtained by a known process, by reacting O-ethyl-S-n-propyl-thiolphosphoric acid diester-amide with orthoformic acid esters at temperatures between 100° and 200° C., if appropriate in the presence of a catalyst, such as, for example, p-toluenesulphonic acid (see U.S. Pat. No. 3,903,207).

O-Ethyl-S-n-propyl-thiolphosphoric acid diester-amide can be prepared from O-ethyl-thiolphosphoric acid ester-amide, which is known, or alkali metal salts thereof by reaction with 1-bromopropane, if appropriate in the presence of a diluent, such as, for example, ethanol, at temperatures between 20° and 100° C.

The ortho-formic acid esters also to be used as starting compounds are known.

Formula (III) provides a definition of the amines to be used as starting materials in the process of this invention. Preferably, in this formula, R has the meaning given as preferred in the case of formula (I).

Examples which may be mentioned are: methylamine, ethylamine, n-propylamine and iso-propylamine.

The amines of the formula (III) are known compounds.

In general, the process for the preparation of the new O-ethyl-S-n-propyl-N-aminomethylidene-thiolphosphoric acid diester-imides (I) is carried out using a diluent. Virtually any inert solvent can be used as the diluent; however, alcohols, for example methanol or ethanol, are preferably used.

The reaction temperature can be varied within a substantial range. In general, the reaction is carried out at temperatures of from −10° to +100° C., preferably from 0° to 50° C. The reaction is in general carried out under normal pressure.

In carrying out the process according to the invention, 1 to 2 moles of amine are generally employed per mole of O-ethyl-S-n-propyl-N-alkoxymethylidene-thiolphosphoric acid diester-imide. In general, the amine is initially introduced in a diluent, and the O-ethyl-S-n-propyl-N-alkoxymethylidene-thiolphosphoric acid diester-imide is added, while cooling with ice, and the reaction mixture is then stirred at room temperature for several hours. The volatile constituents of the reaction mixture are subsequently distilled off in vacuo.

The new compounds are obtained in the form of oils, which cannot be distilled without decomposition, but which can be freed from the last volatile constituents by so-called "incipient distillation", that is to say by prolonged heating to moderately elevated temperatures under reduced pressure. The refractive index is used for their characterization.

The new O-ethyl-S-n-propyl-N-aminomethylidene-thiolphosphoric acid diester-imides (I) are distinguished by an outstanding action in combating pests, but in particular by an insecticidal, acaricidal and nematicidal action. They also have a good root systemic action against sucking and biting insects and mites. The new compounds can thus be employed successfully in the protection of plants for combating animal pests.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and Schistocerca gregaria;

from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca Spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bubalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha,* Amphimallon solstitialis and Costelytra zealandica;

from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culux spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthopodicidal or nematicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) or nematodes which comprises applying to the arthropods or nematodes, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compund according to the present invention, in admixture with a diluent or carrier.

The present invention further provides crops protected from damage by arthropods or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The preparation of the novel compounds is shown in the following illustrative examples:

EXAMPLE 1

(a)

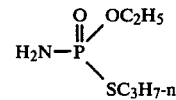

185 g (1.5 mol) of 1-bromo-propane were added to a solution of 272 g (1.5 mol) of the hydrate of the sodium salt of O-ethyl-thiolphosphoric acid ester-amide in 600 ml of ethanol and the reaction mixture was slowly heated to the boil under reflux for four hours, while stirring. It was concentrated in a rotary evaporator and the residue was dissolved in cold water. The mixture was extracted three times with 300 ml of chloroform each time, the chloroform extracts were combined and dried and the chloroform was distilled off under a waterpump vacuum. The product which remained was purified by incipient distillation under a high vacuum. 231 g (84% of theory) of O-ethyl-S-n-propylthiolphosphoric acid diester-amide were obtained. Refractive index: $n_D^{21} = 1.4930$.

(b)
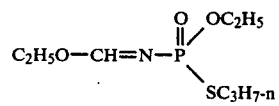

95 g (0.5 mol) of O-ethyl-S-n-propyl-thiolphosphoric acid diester-amide, 100 g (0.66 mol) of ortho-formic acid triethyl ester and 4 g of p-toluenesulphonic acid were heated, while stirring, until a bath temperature of about 150° C. was reached. The alcohol formed as a by-product was distilled off over a 10 cm Vigreux column in the course of the reaction. When the internal temperature had reached about 130° C., the crude product which remained in the flask was purified by distillation under a high vacuum. 100 g (83% of theory) of O-ethyl-S-n-propyl-N-ethoxymethylidenethiolphosphoric acid diester-imide were obtained. Boiling point: 92° C./0.01 mm Hg.

(c)
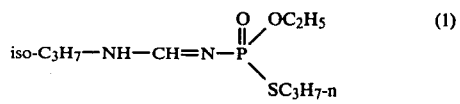

120 g (0.5 mol) of O-ethyl-S-n-propyl-N-ethoxymethylidene-thiolphosphoric acid diester-imide were allowed to run into a solution of 40 g (0.66 mol) of isopropylamine in 250 ml of ethanol of 0° to 5° C. in the course of 30 minutes, while stirring, an exothermic reaction being observed. The reaction mixture was stirred at 20° to 25° C. for three hours. Highly volatile components were then distilled off under a waterpump vacuum and the product which remained was purified by incipient distillation under a high vacuum. 119 g (94% of theory) of O-ethyl-S-n-propyl-N-iso-propylaminomethylidene-thiolphosphoric acid diesterimide were obtained.

Refractive index: $n_D^{26} = 1.4940$.

EXAMPLE 2

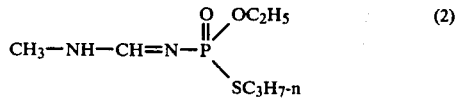

Using 120 g (0.5 mol) of O-ethyl-S-n-propyl-N-ethoxymethylidene-thiolphosphoric acid diester-imide, 30 g (1 mol) of methylamine and 250 ml of methanol, 95 g (85% of theory) of O-ethyl-S-n-propyl-N-methylaminomethylidenethiolphosphoric acid diester-imide were obtained analogously to Example 1.

Refractive index: $n_D^{26} = 1.4927$.

The pesticidal activity of the compounds of this invention is illustrated by the following examples wherein the compounds according to the present invention are each identified by the number (given in brackets) from preparative Examples 1 and 2 hereinabove:

EXAMPLE 3

Test insect: *Phaedon cochleariae* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1) and (2).

EXAMPLE 4

Test insect: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (1) and (2).

EXAMPLE 5

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compounds showed a superior activity compared to the prior art: (1) and (2).

EXAMPLE 6

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (1) and (2).

EXAMPLE 7

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the degree of destruction was determined in %: 100% means that all of the beetle larvae had been killed whereas 0% meant that none of the beetle larvae had been killed.

In this test, for example, the following compounds showed a superior activity compared to the prior art: (1) and (2).

It will be appreciated that the instant specification and examples are set forth by way of illustration and not limitation, and that various modifications and changes may be made without departing from the spirit and scope of the present invention.

What is claimed is:

1. An O-ethyl-S-n-propyl-N-alkylamino-methylidene-thiolphosphoric acid diester-imide of the formula

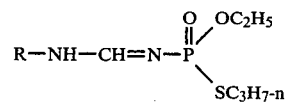

in which R is alkyl.

2. A compound according to claim 1, in which R is alkyl with 1 to 5 carbon atoms.

3. A compound according to claim 1, in which said compound is O-ethyl-S-n-propyl-N-iso-propylamino-methylidene-thiolphosphoric acid diester-imide of the formula

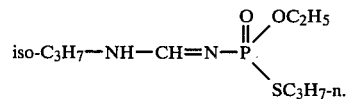

4. A compound according to claim 1, in which said compound is O-ethyl-S-n-propyl-N-methylamino-methylidene-thiolphosphoric acid diester-imide of the formula

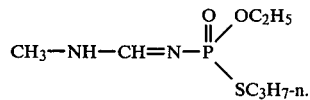

5. An arthropodicidal or nematicidal composition containing as active ingredient an arthropodicidally or nematicidally effective amount of a compound according to claim 1 in admixture with a diluent.

6. A method of combating arthropods or nematodes which comprises applying to the arthropods or nematodes, or to a habitat thereof, an arthropodicidally or nematicidally effective amount of a compound according to claim 1.

7. A method of combating arthropods or nematodes which comprises applying to the arthropods or nematodes, or to a habitat thereof, an arthropodicidally or nematicidally effective amount of a compound according to claim 3.

8. A method of combating arthropods or nematodes which comprises applying to the arthropods or nematodes, or to a habitat thereof, an arthropodicidally or nematicidally effective amount of a compound according to claim 4.

* * * * *